United States Patent [19]

Names

[11] Patent Number: 5,055,047
[45] Date of Patent: Oct. 8, 1991

[54] METAL IMPRESSION CONFIRMATION SYSTEM FOR DENTAL IMPLANTS

[76] Inventor: Curtis D. Names, 305 Saratoga Ave., Los Gatos, Calif. 95030

[21] Appl. No.: 599,294

[22] Filed: Oct. 17, 1990

[51] Int. Cl.[5] .................. A61C 9/00; A61C 11/00; A61C 8/00
[52] U.S. Cl. .................. 433/214; 433/174; 433/213
[58] Field of Search .......... 433/213, 214, 172, 173, 433/174

[56] References Cited

U.S. PATENT DOCUMENTS

| | | | |
|---|---|---|---|
| 2,644,231 | 8/1951 | Brennan | 433/173 |
| 4,003,132 | 1/1977 | Beck | 433/214 |
| 4,708,654 | 11/1987 | Branemark | 433/213 |

OTHER PUBLICATIONS

Dental Implants: Tissue-Integrated Prosthesis Utilizing the Osseointegration Concept, from the Mayo Clinic Proceedings, vol. 61, Feb. 1986, pp. 91–97.

Primary Examiner—John J. Wilson
Assistant Examiner—Cindy A. Cherichetti
Attorney, Agent, or Firm—Robert C. Hill

[57] ABSTRACT

A method and confirmation device for making an accurate impression of the upper or lower teeth, implant and gum assembly in which the device includes a cylindrical section having one end temporarily attachable to the exposed threaded end of the implant and a second end having an opening to receive a guide pin. An elongated wing extends tangentially from the cylindrical surface perpendicular to the axis of the cylinder so that when the cylindrical section is attached to the implant, the wing extends along the gum line and has an end that is rigidly attachable to the cylindrical section of a neighboring confirmation device. A rigid metallic frame is thereby established which serves as a foundation for impression material molded in a dental tray around the frame and dental process comprising the implants and remaining teeth and gums. The frame prevents distortion of the impression material, thereby providing that the molded impression is an accurate form with which a master model of the finished dentures can be made.

3 Claims, 3 Drawing Sheets

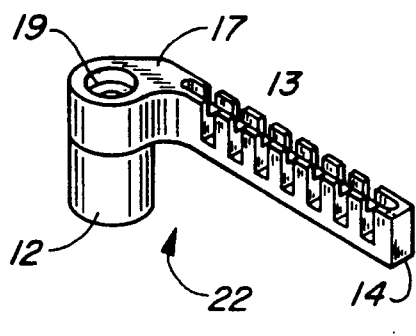
FIG._1A
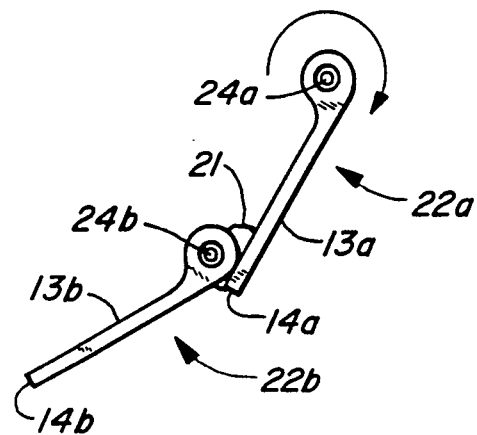
FIG._3
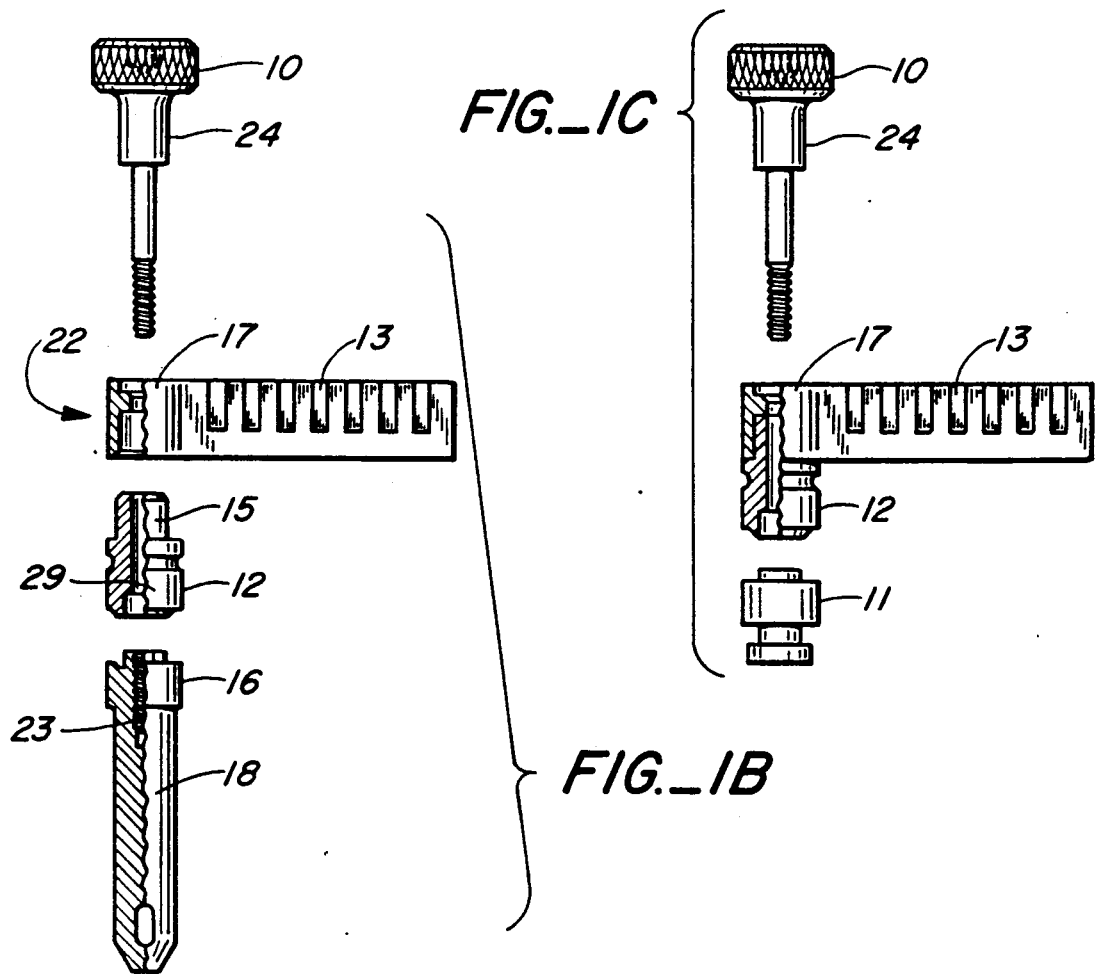
FIG._1B
FIG._1C

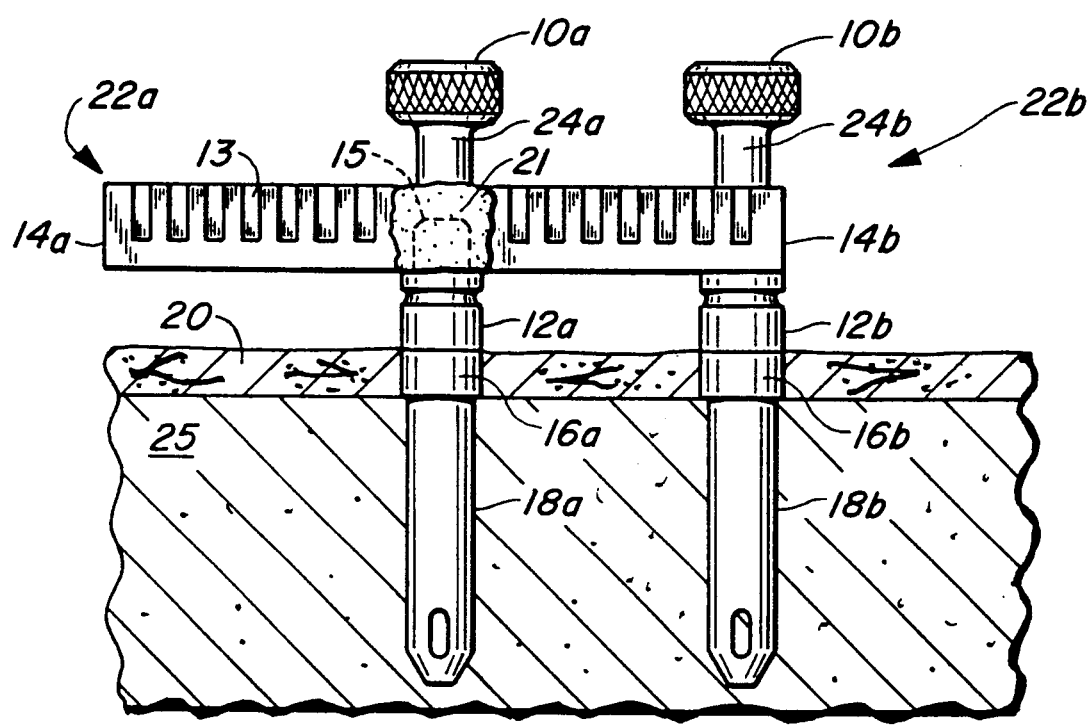
FIG._2
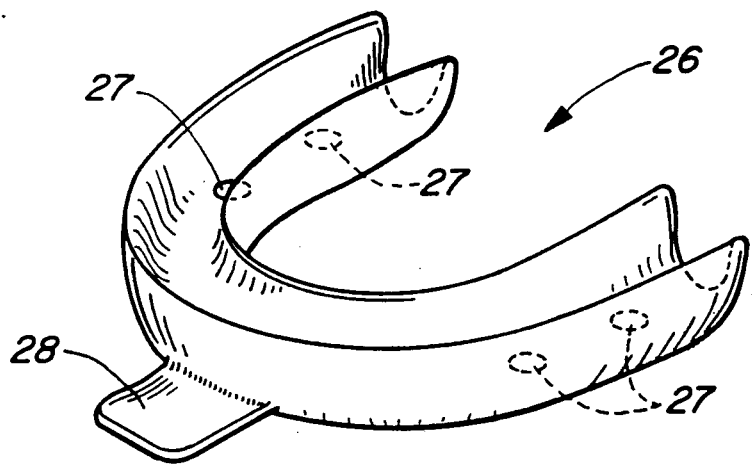
FIG._4

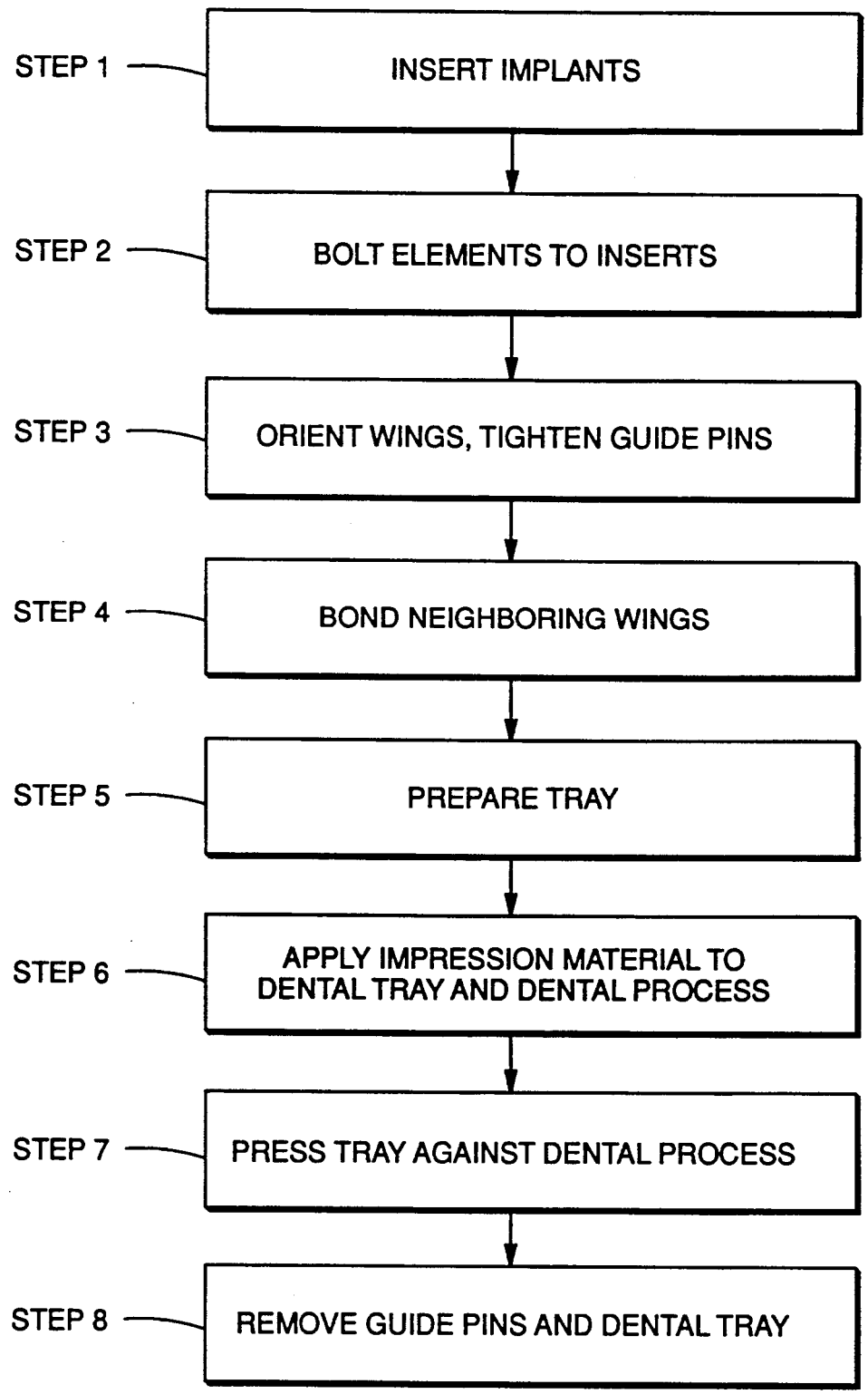
FIG._5

5,055,047

METAL IMPRESSION CONFIRMATION SYSTEM FOR DENTAL IMPLANTS

FIELD OF THE INVENTION

This invention relates to apparatus and methods for forming impressions within the mouth of either the upper or lower teeth and dental implats and particularly to a device and method for making an impression that can be used ultimately to obtain very accurate alignment of neighboring screw connected prosthetic components.

BACKGROUND AND INFORMATION DISCLOSURE STATEMENT

Osseointegrated dental implants, an alternative to a single tooth, fixed bridge or removable dentures, have been developed as the result of the discovery by Dr. Branemark in Sweden of the ability of bone to make direct biological attachment to the surfaces of titanium implants. (See "Dental Implants: Tissue-Integrated Prosthesis Utilizing the Osseointegration Concept" published in the Mayo Clinic Proceedings, vol. 61 Feb. 1986, pp 91–97).

The procedure involves two operations.

The first operation involves surgically exposing the bone and then drilling the surface of bone where the prosthetic tooth is to be attached and inserting an implant (a titanium anchor) having a threaded or non-threaded plug into the hole in the bone. A flap of skin is then sewn over the site. During the healing period that follows, the bone becomes biologically attached to the surface of the implant.

In the second operation, after the implant has become thoroughly attached to the bone, the flap is removed. An abutment, which is simply an anchoring stud that serves as a spacer, is screwed onto the implant for ultimate attachment to the prosthetic tooth.

In order to achieve the desired arrangement of prosthetic teeth in the mouth, a "negative" impression is made of the dental process which includes the implants, remaining teeth and gums. In this procedure, a "coping" (temporary stud) is attached at the site of each individual implant in place of the threaded plug. An impression material contained in an impression tray is imposed around the coping and dental process. The impression material hardens and then the tray with impression material is removed. U.S. Pat. No. 4,693,683 to Lee and U.S. Pat. No. 4,432,728 to Sharkey describe dental trays and techniques for making impressions of dental processes.

Either one of two types of copings is used, a "Square coping" or a "Round coping". These copings are described as follows:

The square coping is used with a custom made impression tray that has an opening that allows access to a placement pin that attaches the square coping through a temporary or "analog" abutment to the implant. After the impression material has set, the placement pin is removed thus permitting removal of the custom tray from the patient's mouth with the square coping imbedded in the impression material. A positive stone cast model of the patient's dental process is made in which an "analog" abutment (a substitute for the final abutment in the patient's mouth,) is temporarily attached to the square coping while the master model is being formed around the negative impression.

A disadvantage with the square coping is that it will move within the impression material when placing a guide pin and analog abutment together despite efforts such as intertwining dental floss between copings.

The round coping is placed directly on the implant. A tray with impression material is then placed over the round coping and after the impression material has hardened, the tray and material are removed leaving the round coping still on the implant. The round coping must be reinserted into the molded impression in order to make the master model.

A disadvantage with the round coping is that there is a technique difficulty in returning the coping fixture into the impression material in a precise fashion.

The problem with the use of square and round copings is exaccerbated by distortion of the impression material as the material sets. The distortion is directly proportional to the mass of the material mass, i.e., the greater the mass, the greater the distortion.

The result of these problems is that the use of copings to form dental implant impressions, although long practiced, rarely produces an accurate impression.

THE INVENTION

Objects

It is an object of this invention to provide a new and improved apparatus and method for forming an accurate impression of dental implants.

Another object is to establish location of surgically placed implants for the purpose of taking an impression of the implants for prosthetic restoration.

Another object is to retain alignment of implants relative to one another without the distortion associated with the use of impression material experienced using methods of the prior art.

Another object is to provide the means to confirm that the locations of the implants in the master cast model are the same as the location of the implants in the patient.

Another object is to provide a device for forming an impression which is sturdy in construction for convenient use by dental or laboratory personnel.

Summary

This invention is directed toward a metallic impression confirmation system which uses a metallic frame comprising individual foundation elements that are attachable to each implant. The frame provides a rigid base around which an impression material may be molded. The molded impression retains dimensional stability by virtue of the rigidity of the frame.

Each foundation element of the frame comprises a base member with a bore so that a threaded guide pin (bolt) through the bore screws into the implant allowing aligned attachment of the base to an implant. An elongated rectangular wing has one end attached tangentially to the surface of the cylinder and extends along the gum line. The opposing end of the wing may be rigidly bonded to a neighboring foundation element with a small amount of resinous bonding material. After assembly of the frame in the patient's mouth, impression material is injected around the dental process and a dental tray is pressed onto the overcoated dental process. The impression material hardens in place. Openings in the tray permit removal of each guide pin attaching an element to an implant so that the tray and mold assembly can be removed from the mouth with the frame of metallic confirmation devices imbedded in the hardened impression material. The molded tray, frame and impression material assembly is then used to make a master casting of the patient's dental process and prothesis.

DRAWINGS

FIG. 1a is a perspective view of a metallic impression confirmation element attachable to an implant for forming the metallic impression confirmation frame.

FIG. 1b is an exploded side view of the element of FIG. 1a in between a threaded guide pin having a hex head and an implant.

FIG. 1c is an assembly side view of an element of FIG. 1a in between a threaded guide pin and an analog abutment.

FIG. 2 is a perspective view showing two neighboring foundation elements, each attached to implants imbedded in jaw bone, shown cutaway to reveal the implant, bone and gumline.

FIG. 3 is a top view of the two adjoined foundation elements of FIG. 2.

FIG. 4 is a perspective view of a tray showing holes to provide access to the heads of the guide pins when the tray is in position over the implants.

FIG. 5 is a flow chart of the method of making an impression of a dental process in accordance with the practices of the invention.

DESCRIPTION OF THE PREFERRED EMBODIMENT

The following detailed description illustrates the invention by way of example and not by way of limitation of the principles of the invention. This invention will clearly enable one skilled in the art to make and use the invention according to what I presently believe is the best way to carry out the invention.

Turning now to a discussion of the drawings, the novel foundation element for making reinforced impressions of the present invention is generally indicated as item 22 in FIGS. 1, 2 and 3.

As shown in the assembly view of FIG. 1a, the foundation element has a cylindrical base 12 attached to one end of a rectangular elongated wing 14. A coaxial bore 19 in the cylindrical base 12 is perpendicular to the wing 14 into which may be inserted a connecting pin 24. (The connecting pin 24 is shown in FIG. 1b.)

FIG. 1b shows an exploded view of the element 22 to show that the cylindrical base 12 has a support 29 and neck section 15 that presses into a sleeve section 17 on the end of the wing 14. Both cylindrical base 12 and sleeve section 17 are partially cutaway in FIG. 1b to illustrate that neck 15 may be pressed into sleeve 17 as shown also in FIG. 1c, also partially cutaway.

As shown in FIG. 1b, the cylindrical base may be screwed onto a standard abutment 16, which is the intermediate connector between the implant 18 and the prosthetic tooth (not shown.) Standard abutment 16 is also partially cutaway to reveal thread 23.

Alternatively, as shown in FIG. 1c, the cylindrical base 12 may be attached to a standard Branemark abutment analog 11 which is used as a replica of the implants in a fabricated artificial stone model of the dental process.

FIG. 1b and 1c show the analog abutment manufactured by Branemark. It should be understood that other implant companies such as IMZ or Steri-oss manufacture their own matching implants and analog abutments The guide pin 24 has a knurled hex head 10 on one end and is threaded on the other end for insertion through the bore 19 and attachment to abutment 16 or abutment analog 11.

The cylindrical base 12 is preferably made of titanium which is a non contaminating material that is compatible with the interfacing titanium implants.

The wing 14 is made of stainless steel in preference to titanium because it is harder than titanium and can be used repeatedly with bonding materials well known in the dental art such as light-cured composites (sold by Premiere and 3M), self cured resins (Dura-lay manufactured by Reliance and Relate manufactured by Parkell) and acrylics (Microlon manufactured by Hygenic) when it is required to bond neighboring elements together as discussed as follows.

As shown in the side view of FIG. 2 and the top view of FIG. 3, when two elements 22a and 22b are adjacent to one another in neighboring implants, 16a and 16b inserted into bone 25, the elements are oriented so that the wings extend along the gum line 20. Wing 14b is shown contacting the neighboring element to which it is bonded by a bonding resin 21 thereby forming the rigid frame. The wings have grooves 13 along their sides. The purpose of the grooves is to provide for a reservoir of a resin 21 that bonds the wing 14b to the neighboring element 22a.

The wings 14 of the elements can be modified in length in accordance with the distance between implants by cutting with a carborundum cutting disk.

FIG. 3 shows a top view of two elements attached to adjacent implants and shows that the wing 14a is pressed against the neighboring element 22b when the knurled hex head 10a is turned in the clockwise direction to tighten the guide pin. Bonding resin 21 secures the two elements together.

Viewed from the topside of the elements shown in FIG. 3, the wing is offset from the base and extends tangentially in the topside around the base. This construction provides that each element may lie against a neighboring element yet lie within the dental tray and within the dental arch. The clockwise arrangement of the wing with respect to its neighbor provides that the dentist can begin by tightening the fartherest right wing against the base of the next fartherest right element, etc.

After the frame of elements has been secured to the implants, impression material is applied to the dental process. A dental tray 26 is prepared as shown in FIG. 4. The dental tray 26 is shown to be curved trough with holes 27 drilled into the tray at locations corresponding to the positions of the implants. A tab 28 is provided for easy positioning in the patient's mouth. The interior surface of the tray is first lined with an adhesive and then filled with additional impression material prior to pressing the tray against the dental process.

The steps included in the method of making an impression according to this invention are illustrated in the flow diagram of FIG. 5.

In step 1, dental implants are implanted in the gums and the implants are exposed in accordance with well known procedures discussed in the BACKGROUND.

In step 2, a foundation element is bolted to each implant by inserting a threaded guide pin through the bore of the cylindrical base and screwing into the abutment of the implant.

In step 3, the wing of each element is oriented to touch its neighbor in the clockwise direction and the guide pins are tightened.

In step 4, the wing is bonded to its neighbor by an appropriate bonding resin thereby forming a rigid frame.

In step 5, a dental tray is prepared by cutting access holes in the dental tray corresponding to locations ultimately adjacent to the implants and the inside of the tray is lined with adhesive.

In step 6, pliable impression material is applied to the dental process including the implants and rigid frame and the dental tray is also filled with impression material.

In step 7, the tray is pressed against the dental process and the heads of the guide pins are exposed through the access holes in the tray.

In step 8, after the impression material has hardened, the guide pins are removed and the impression is removed from the mouth.

In the foregoing paragraphs, a method for making an impression of a dental process with implants has been described which meet the objects of the invention. A rigid frame is constructed using an element attached to each implant and bonded to its neighboring element. The frame provides reinforcement of impression material molded to the frame and dental process and thereby prevents distortion of the hardened impression material. The reinforced molded impression is a sturdy reliable form that may be used as a negative in the construction of a master cast model. Each wing, perpendicular to the axis of its implant, is a guide that indicates alignment between neighboring implants. The result is that misalignment of prothesis is avoided such as occurs with techniques and methods of the prior art.

It should be understood that various modifications within the scope of this invention can be made by one of ordinary skill in the art without departing from the spirit thereof.

The essential feature of this invention is an elongated wing member with means for attaching one end of the wing to the implant such that the long dimension of the wing lies along the gum surface and thus provides that neighboring elements can be interconnected. Means other than the two piece element discussed above could include a one piece elongated element simply having a bore in the first end for inserting a guide pin.

Although the foregoing examples were illustrated by use with a Branemark implant, it will be understood that, with appropriate modification, the invention can be used with implants manufactured by other companies. The base must be modified to interface with the implant selected from those manufactured by the other companise.

As another example of modification, although the base in the Preferred Embodiment is cylindrical, a base having another shape, e.g., a rectangular block, could be used.

I claim:

1. A foundation element for reinforcing an impression of a dental process including at least one implant with a threaded hole, said element comprising:

a base member having a neck section contiguous with a support section and a straight bore through both sections;

an elongated wing having a long dimension with a first end and a second end;

a sleeve attached to said first end with a bore perpendicular to said long dimension of said wing;

said sleeve bore dimensioned to be pressed onto said neck section thereby providing that a screw may be inserted through said bore in said base from said neck section to said support section and screwed into said threaded hole of said implant;

said second end of said wing touching a neighboring foundation permitting said second end to be bound to said neighboring element with bonding resin; and, said wing having a surface with grooves thereby providing a reservoir for anchoring said bonding resin.

2. A method for making a impression of a dental process having a plurality of implants which includes the steps:

(a) attaching to at least two implants a foundation element which includes an elongated wing member having an end attached to a base with a bore, said bore providing that said element may be attached to said implant by a screw extending through said bore, screwed into said implant;

(b) applying a bonding resin to a location on said wing;

(c) orienting said wing about said screw to a position where said wing contacts a neighboring foundation element thereby forming a rigid frame of said bonded foundation elements;

(d) tightening said screw extending through said bore and screwed into said implant thereby firmly securing said foundation element to said implant;

(e) cutting at least two holes in an impression tray, each hole located to provide access to said heads of said screws when said tray is placed around said dental process;

(f) coating impression material onto said dental process and said attached foundation elements;

(g) placing said dental tray containing additional impression material around said coated dental process and allowing said impression material to cure;

(h) unscrewing and removing said screws through said access holes thereby detaching said impression from said dental process; and (i) withdrawing said impression including said tray with said impression and said foundation elements imbedded in said impression material.

3. A method as in claim 2 which includes after step (e) an additional step:

coating a surface of said tray to be opposed to said dental process with an adhesive thereby strengthening bonding between said tray and said impression material to be applied in step (f).

* * * * *